Figure 1:
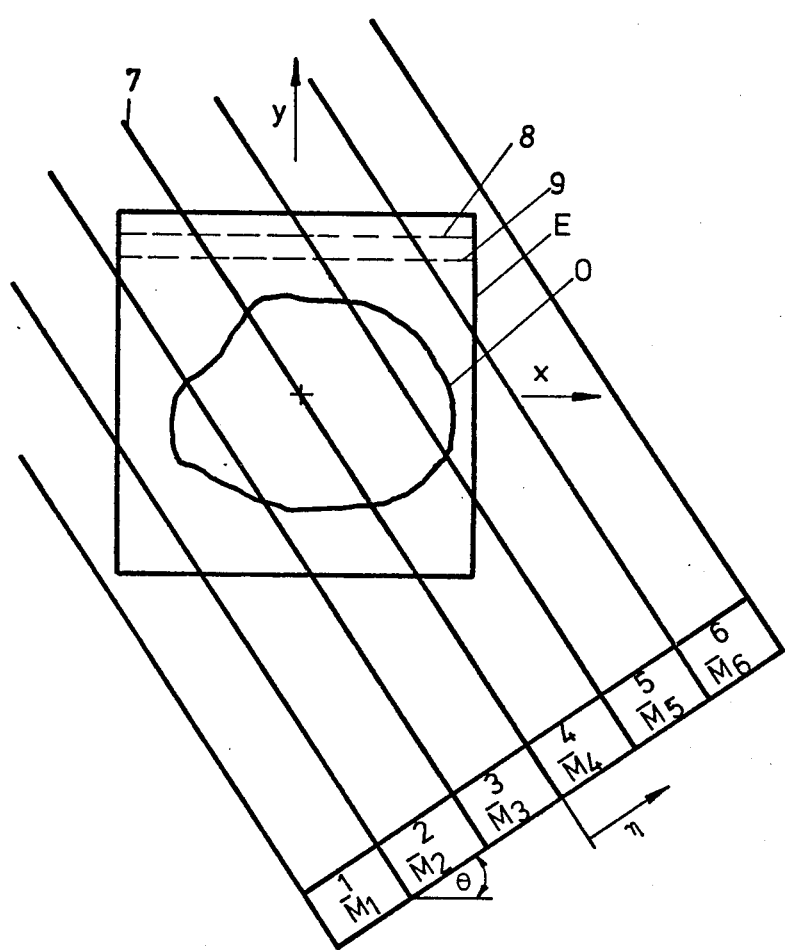

United States Patent [19]

Kowalsi

[11] 4,167,039

[45] Sep. 4, 1979

[54] DEVICE FOR MEASURING THE DISTRIBUTION OF THE ABSORPTION OF THE EMISSION OF RADIATION IN A LAYER OF A BODY

[75] Inventor: Gunter Kowalsi, Hamburg, Fed. Rep. of Germany

[73] Assignee: U.S. Philips Corporation, New York, N.Y.

[21] Appl. No.: 885,299

[22] Filed: Mar. 10, 1978

Related U.S. Application Data

[63] Continuation of Ser. No. 685,271, May 11, 1976, abandoned.

[30] Foreign Application Priority Data

May 13, 1975 [DE] Fed. Rep. of Germany ....... 2521171

[51] Int. Cl.$^2$ ................................................ G01T 1/29
[52] U.S. Cl. .................. 364/515; 250/445 R; 364/414; 364/555
[58] Field of Search ............... 364/414, 525, 527, 514, 364/515, 555; 250/272, 308, 510, 550, 445 R, 445 T, 363 S, 369

[56] References Cited

U.S. PATENT DOCUMENTS

| 3,878,373 | 4/1975 | Blum | 364/414 |
|---|---|---|---|
| 3,940,599 | 2/1976 | Hounsfield et al. | 364/527 |
| 3,955,086 | 5/1976 | Tsujii et al. | 364/525 |

*Primary Examiner*—Charles E. Atkinson
*Assistant Examiner*—Errol A. Krass
*Attorney, Agent, or Firm*—Thomas A. Briody; Edward J. Connors, Jr.; Jack E. Haken

[57] ABSTRACT

In devices for reconstructing the adsorption distribution in a layer of a body on the basis of the measuring values obtained by means of a CT scanner, the measuring values (or values derived therefrom) are "spread" along strips which occupy the same position relative to the image plane as the strips along which the measuring value were obtained. The invention assigns the measuring values to individual image elements, the calculation of weighting factors being eliminated by subdividing each image element into smaller image points (9 to 16 times smaller).

8 Claims, 5 Drawing Figures

DEVICE FOR MEASURING THE DISTRIBUTION OF THE ABSORPTION OF THE EMISSION OF RADIATION IN A LAYER OF A BODY

This is a continuation of application Ser. No. 685,271, filed May 11, 1976, now abandoned.

The invention relates to a device, commonly known as a CT scanner, for determining the spatial distribution of the absorption or the emission of radiation in a layer of a body, the absorption or the emission of the body being measured in a large number of measuring series in a large number of directions in the layer by means of a radiation source and a detector, each measuring series producing a number of measuring values of the absorption or the emission in strips which extend at least approximately parallel relative to each other, the absorption or the emission being calculated and displayed in image points of the layer on the basis of the said measuring values. This device is preferably used for X-ray diagnosis or nuclear medicine.

As used herein, the term:
"measuring value" means the value of the absorption along a straight line or strip through the body;
"measuring series" refers to a group of measuring values taken along parallel (or at least approximately parallel) lines or strips; and
"signal values" includes both measuring values and values derived therefrom, either alone or in combination with other measuring values in a measuring series (i.e. by a process of convolution).

A device of this kind is known from German Offenlegungsschrift No. 1,941,433. The absorption in a (human) body is measured by means of a radiator which is displaced, together with a radiation detector which measures the radiation behind the body, perpendicularly to the direction of the radiation. The detector thus measures a measuring series for the absorption of the radiation along the straight lines through the body which extend parallel to each other and which are determined by the position of the radiator and the detector. After such a measuring series, the radiator/detector system is rotated and a further measuring series is completed at a different angle relative to the body, etc. The absorption in the individual points or regions in the layer covered by the measurement cannot be simply reconstructed from the measuring values obtained, because the measuring values do not represent a measure of the absorption at individual points, but rather of the absorption along a straight line or strip through the body. From a mathematical point of view, this implies that the value of a function (absorption, emission, density, etc.) in individual points of the layer defined by the straight lines must be calculated from the line integrals of this function along a large number of intersecting straight lines.

This problem is also encountered in the measurement of the radioactivity distribution in radioactively marked biological objects, in the calculation of layers of macromolecules (viruses and the like) measured by means of an electron microscope, and also in the examination of layers of technical objects (for example, materials testing) by means of penetrating radiation. The reconstruction of the absorption in the layer is effected in known devices in that the layer to be examines is subdivided into a matrix of square image elements, the dimensions of which correspond approximately to the width of a strip. Each image element is assigned the signal value in each measuring series which has been measured in the strip in which the image element is situated. If it is assumed that the image element and the strip have approximately the same width, an image element can be influenced by as many as three signal values which represent the absorption of the radiation in three parallel strips. The signal value consequently, is multiplied by a weighting factor during the calculation of an image element, the said factor corresponding to the common plane of the strip and the image element.

This method, performed in a computer, involves very long computing times and a very expensive computer, notably for the calculation of the weighting factors.

In order to realize a shorter computing time by means of a simpler device, it has already been proposed to superpose values derived from the measuring values by a convolution process along adjoining strips, on the target of a charge storage tube, the position and the direction of the said strips corresponding to the position and the direction of the strips during the formation of the assigned measuring values. However, serious signal-to-noise ratio problems are then encountered.

The invention has for its object to realize fast processing of the measuring values by simple means and without deterioration of the signal-to-noise ratio.

To this end, an allocation device is provided which assigns a signal value, to each image point of the layer to be examined for each measuring series, the said value having been obtained in a strip in which the relevant image point is situated, the values assigned to the image points from all measuring series being stored and superposed in a storage and summing device, the superposed values being displayed by means of a display device as the mean value of the absorption or the emission in different adjacent image points in the region determined by these image points being displayed.

The invention will be described in detail hereinafter with reference to the drawing.

Figure 2:
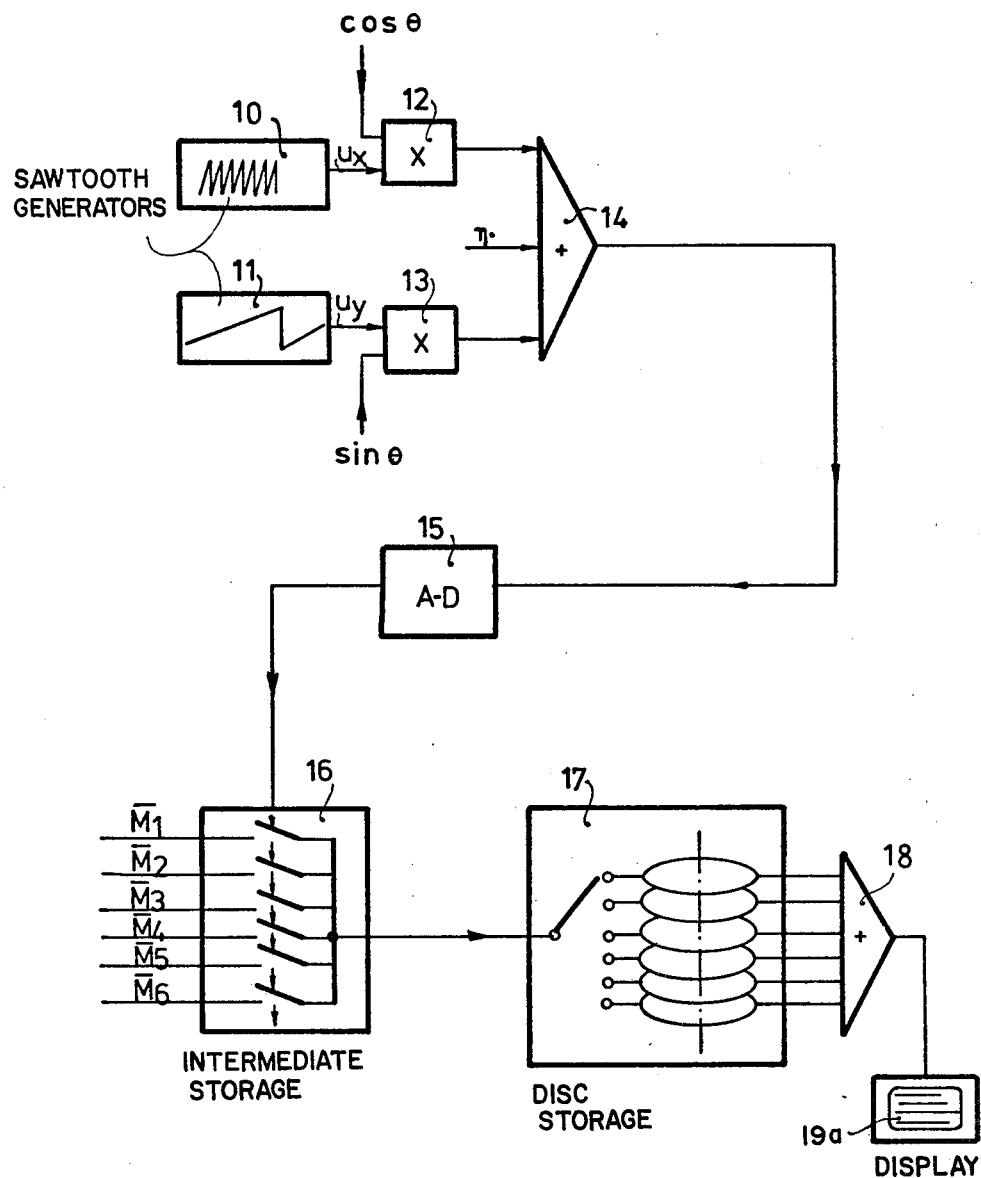
Figure 3:
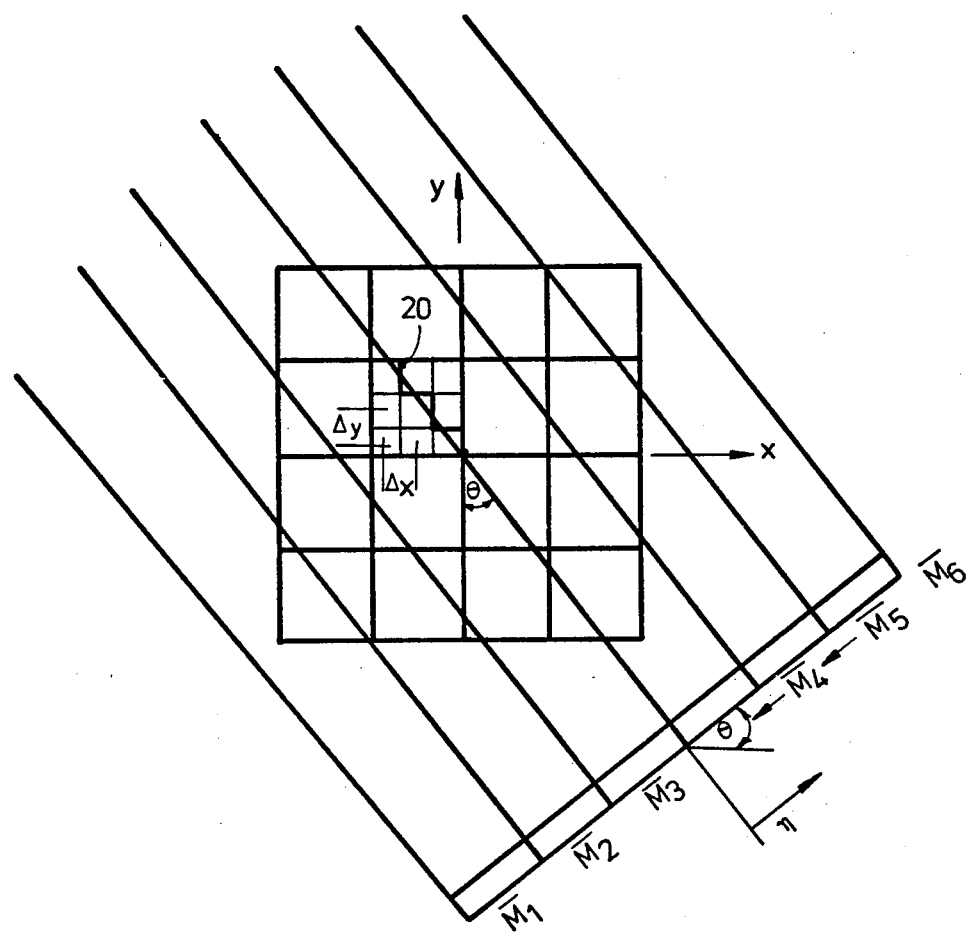
Figure 4:
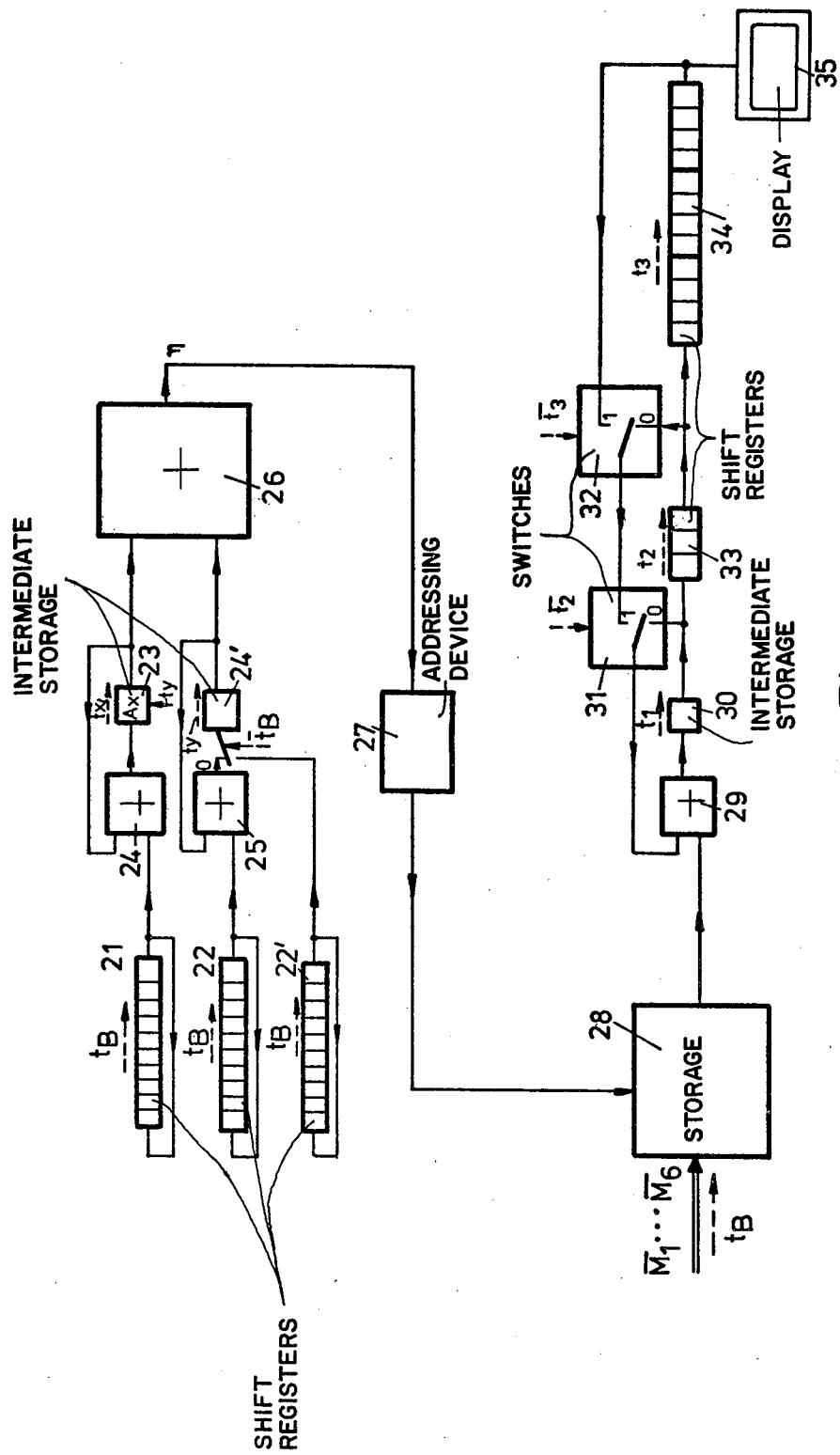
Figure 5:
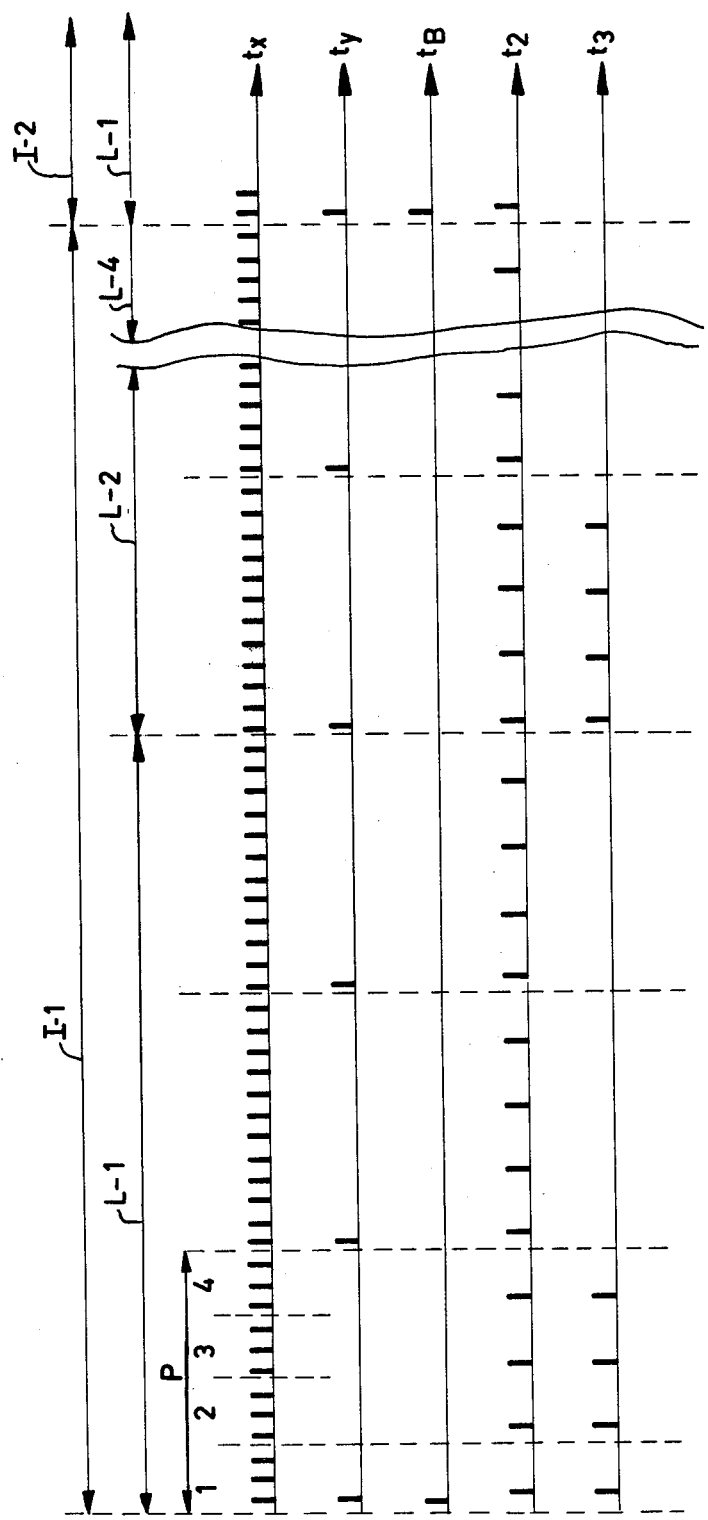

FIG. 1 shows the geometrical lay-out of the strips and the layer to be examined, FIG. 2 shows a first embodiment in accordance with the invention, FIG. 3 shows the geometrical lay-out of the strips, the layer to be examine and the image points for the embodiment shown in FIG. 4, FIG. 4 shows a further embodiment, and FIG. 5 shows the appearance in the time of the clock pulses in the device shown in FIG. 4.

The absorption of the object O in the layer E is determined by way of a large number of measuring series, the absorption being measured in each series along a number of parallel strips. FIG. 1 shows these strips 1 . . . 6 for a measuring series. The absorption in each of these strips is represented by a measuring value. Each measuring value is subsequently subjected to a convolution process, so that the signal values $\overline{M}_1 \ldots \overline{M}_6$ thus calculated depend on the weighted sum of all other measuring values in the measuring series.

The calculation of the absorption from these signal values $\overline{M}_1 \ldots \overline{M}_6$ is effected in that the values are "spread" across the region of the layer to be examined, the said region being covered by the associated strip; for example, the value $\overline{M}_2$ is assigned to the part of the layer which is covered by the strip 2. Consequently, the position of a point in the layer determines which value $\overline{M}$ is assigned to that point. Subsequently, the values derived from a further measuring series are similarly assigned, the said values being superposed on the previously assigned values.

The assignment of a point of the layer to a strip is effected by means of a computer which calculates, on the basis of the position of that point in a fixed x, y system of co-ordinates, its relationship with one of the strips. The association of a point of the layer with a given strip is dependent of the distance $\eta$ (see FIG. 1) between a straight line which passes through the point, parallel to the strip, and the co-ordinate origin (x=0, y=0), the said distance being calculated from the formula:

$$\eta = x \cdot \cos\theta + y \cdot \sin\theta \quad (1)$$

Therein, x and y represent the position of this point in the x, y system of co-ordinates, whilst $\theta$ is the angle at which the strips intersect the x-axis. The distance $\eta$ is calculated for each individual point of the layer, it then being possible to calculate directly the strip whose signal value (for example, $\overline{M}_5$) is to be assigned to the point (the relationship between the distance $\eta$ and the strip whose value $\overline{M}$ is to be assigned to points at the distance $\eta$ is illustrated by FIG. 1).

FIG. 2 shows a device in accordance with the invention which is constructed on the basis of the foregoing considerations. The device comprises two sawtooth generators 10 and 11 which generate two sawtooth signals $u_x$ and $u_y$ of different frequency. If it is assumed that the values of $u_x$ and $u_y$ are proportional to the distance x and y, respectively, from the co-ordinate origin, the output signals $u_x$ and $u_y$ of the sawtooth generators 10 and 11 represent a quantity which line-wise scans the layer to be examined (FIG. 1 shows only two lines 8 and 9).

It is important that the distance between two adjacent lines is substantially smaller, for example, by a factor 3 or 4, than the width of a strip. In the configuration shown in FIG. 1, in which the width of the layer corrjesponds to four strip widths, this means that the layer must be scanned by approximately 12 to 16 lines. This implies that the period of the signal $u_y$ must be 12 to 16 times larger than the period of the signal $u_x$. In practice, the layer is not scanned along six rather wide strips, as is shown in FIG. 1, but along a large number of strips, for example 150 strips. The number of lines must then be accordingly larger (450 to 600) so that the horizontal and vertical deflection generators (the latter generators scanning 625 lines) of the type commonly used in a television apparatus are suitable for use as the sawtooth generators 10 and 11.

The output signals $u_x$ and $u_y$ of the sawtooth generators 10 and 11, respectively, are each applied to the inputs of a multiplier circuits 12 and 13, respectively, the other input of each of said multiplier circuits carrying a voltage which is proportional to $\cos\theta$ and $\sin\theta$, respectively. The output signals of the multiplier circuits 12 and 13 are added in an adding circuit 14 in which an additional value $\eta_0$ is added so that, taking into account the equation (1), the output of the adding circuit 14 carries a signal which is proportional to $\eta + \eta_0$. This signal is applied to an analog-to-digital converter 15 which converts the output signal into a digital number. When the proportions are suitably chosen, the digital output signal represents the number of the strip or the address of the storage location in which the signal value obtained in this strip is stored.

EXAMPLE

It is assumed that the distance y or x=1 from the co-ordinate origin corresponds to the width of the strip. It is also assumed that the value x or y=1 corresponds to the signal $u_x$ or $u_y=1$ V, and that no further proportionality factors are introduced by the multiplier circuits 12 and 13 and the adding circuit 14, so that, for example, for $\theta=0$, x=0.5, a voltage of 0.5 V is present on the output of the adding circuit 14, the value corresponding to $\eta_0$, assumed to be 4 V, being added thereto. If a voltage of, for example, 4.5 V has thus been generated, it will be converted into the numerical term 4.5 by the analog-to-digital converter 15, however, this converter 15 is constructed so that the last decimal position is eliminated, so that on the output of the converter 15 the number 4 is present which, if the values $\overline{M}_1 \ldots \overline{M}_6$ are correctly assigned to the storage position, denotes the address of the storage position in which the value $\overline{M}_4$ assigned to the strip 4 is stored. Because the sawtooth voltage $u_x$ increases, the output voltage always increases and exceeds the voltage value 5 V at a given instant, for example, when for $\theta=0$ the value x becomes larger than 1. The number 5 then appears on the output of the analog-to-digital converter 15, which means that the address of the store in which the value $\overline{M}_5$ assigned to the fifth strip is stored is addressed. Generally, the analog signal is converted into a digital value for which the above considerations are also valid.

The addressing device formed by the analog-to-digital converter 15 controls an intermediate storage device 16, the various storage positions of this store storing the signal values in the individual strips so that each time the contents of the addressed storage position are available on the output of the intermediate storage device 16.

The intermediate storage device 16 can be replaced be controlled multiplex access to data present in analog form. The value fetched each time from the intermediate storage device 16 in this manner is written on a disc 17 which simultaneously synchronizes the sawtooth generators 10 and 11. The signal values, of a single measuring series assigned to the individual points, are written on a single track in this disc 17.

For the next measuring series, the strips the intersecting the layer to be examined at a different angle $\theta$, for example, a process computer introduces new values sin $\theta$ and cos $\theta$ (for this reason, the multiplier circuits 12 and 13 are preferably constructed as multiplying analog-to-digital converters), and the signal values, which are obtained in this series and which usually deviate from the signal values, of the preceding series are written in the intermediate storage 16. These new signal values, are assigned to the layer, one point after the other, and are stored accordingly in the next track of the disc 17.

This is repeated for all measuring series, so that the number of tracks of the disc 17 should correspond at least to the number of measuring series recorded.

When all measuring series have been processed and recorded on different tracks in the disc 17 in this manner, all tracks are simultaneously read during a read operation. The signals read are added in an adding circuit 18 and are applied to a display apparatus 19a, for example, a television monitor. This display apparatus has a limited resolution so as to achieve the blurring of the various lines to form an image element. The limit of the resolution could possibly be imposed by a strip width; so that the width of the lines scanning the layer is smaller, for example, by the factor 3 to 4, than the resolution of the display apparatus 19a.

Thus, far, it has been assumed that the absorption is measured in exactly parallel strips within a measuring series. However, there are also devices for measuring the absorption in a layer of a body in which a large number of detectors cover the flared radiation behind the object. In those devices, the strips in which the absorption is measured diverge from the radiator. In such a case, the equation (1) must be replaced by $$\eta(x,y) = \frac{x \cdot \cos\theta + y \cdot \sin\theta}{1 + \epsilon(x \sin\theta - y \cos\theta)} \qquad (2)$$

wherein $\epsilon$ describes the divergence of the radiation beam and is to zero in the case of parallel projection. In the case of such spreading the adding circuit 14 must be replaced by an analog computing network which reproduces the formula (2).

In the described embodiment in accordance with the invention, each point of the layer to be examined is *continuously* assigned the signal value ($\overline{M}_1 \ldots \overline{M}_6$) measured along the strip in which the relevant image point is situated. The formation of the mean value of the absorption in different adjacent image points and the display of this mean value in the region determined by these image points is also continuously determined, in that the image, as a super position by means of the adding circuit 18 which adds the video signals of the individual tracks, and the limited resolution display device 19a.

FIGS. 3, 4 and 5 show a further embodiment in accordance with the invention.

In order to assign the strips obtained by the "spreading" of the measuring values to an image matrix representing the layer to be examined, (FIG. 3 is based on an image matrix of only 4×4 quadratic elements) each element, whose dimensions correspond approximately to the width of a strip, is again subdivided into a matrix of points as shown in FIG. 3 which illustrates this subdivision for one element. These points are assigned, without interpolation, to the strip in which they are situated. As a result, the exact movement is replaced by an approximative movement as is indicated in FIG. 3 by the heavy, stepped line 20. Generally, a sub-division of an element into 3×3 points suffices. The number of image points whereto a signal value is assigned is thus increased by a factor 9, but each point is assigned to only one strip. Calculation of weighting factors is thus avoided.

FIG. 4 shows a device for realizing a fast reconstruction of the absorption values in the layer to be examined; FIG. 5 shows the associated clock signals. The device comprises two units, one of which effects the assignment of a signal value to a point of the layer, while the other unit calculates the mean value of the absorption of an element on the basis of the values assigned to the individual points of that element and, after this has been done for all measuring series, superposes and displays the mean values assigned to that image element.

The assignment of an image point to a strip, i.e. to a signal value is defined by the equation (1) when parallel projections are assumed. In the case of a flared projection, the distance is calculated in accordance with the equation (2). If the strip width $\Delta\eta=1$ is chosen by appropriate standardization, the result of the equation (1) merely need be rounded off to an integer in order to produce the number (address) of the intermediate storage position in which the measuring signal value measured in the strip is stored. If the constant value 0.5 is added to the numerical value of the equation (1), rounding off in the upward or downward direction is replaced simply by elimination of the positions behind the decimal point. FIG. 4 can be described on the basis of this consideration.

The addends $\Delta x \cos\theta$ and $\Delta y \sin\theta$ are prepared by two shift registers 21 and 22 whose contents are cyclically advanced per image by a clock signal, $\Delta x$ representing the distance between two points in the x-direction, and $\Delta y$ representing the distance between adjacent points in the y-direction. However, these addends can also be calculated by a process computer. This is particularly advantageous when the angles at which the radiation passes through the layer to be examined during the measuring series have not been predetermined.

When all points are sequentially processed line-wise, the value $\eta$ for each new point must be increased by the addend $\Delta x \cos\theta$ and for each new line by the addend $\Delta y \sin\theta$, starting from initial values $x_0$, $y_0$ which correspond to the co-ordinates of the first point of a line or of an image and which have been written in the mono-cell intermediate stores 23 and 24' by the clock signals $t_y$ and $t_B$. This is effected by means of three adding circuits 24, 25 and 26. In the adding circuit 24, in conjunction with the store 23 whose output is fed back to an input of the adding circuit 24, the clock pulse $t_x$ generates a (preferably digital) signal whose instantaneous value varies in accordance with the co-ordinates of the points on a line. This step-wise increasing signal is returned to the initial value $x_0$ by the clock signal $t_y$ after each line. In the adding circuit 25, the same clock signal generates, in conjunction with the intermediate store 24', a signal which increases in phase and which corresponds to the y-co-ordinate of the relevant line (y perpendicular to the line direction). Each time when all image points of the layer have thus been treated, the storage 24' is returned to its initial value $y_0$ by the signal $t_B$.

The initial values $x_0$ and $y_0$ are dependent of the angle $\theta$; however, an initial value can always be chosen at random, for example $x_0=0$, it then being necessary to change the other value accordingly. This other initial value can be given in advance by the device which also supplies the addends $\Delta x \cos\theta$ and $\Delta y \sin\theta$, i.e. by a shift register 22' which comprises a number of storage cells which corresponds to the number of measuring series and whose contents are cyclically circulated by the clock pulse $t_B$.

The output signal of the intermediate storage devices 23 and 24' is applied to both inputs of an adding circuit 26, the output signal of which controls an addressing device 27. In the case of a digital output signal of the adder the least significant bits of the digital signal can be omitted if correct standardization and generation of the address are chosen. If the signal which represents the distance $\eta$ is present in analog form, the addressing device must comprise an analog-to-digital converter (as described with reference to FIG. 2).

The device described below could, in principle, be constructed as shown in FIG. 2. The embodiment shown in FIG. 4, however, digitally processes the values $\overline{M}_1 \ldots \overline{M}_6$.

The address formed by the addressing device 27 is used for directly actuating a random access intermediate store 28 in which the values $\overline{M}_1 \ldots \overline{M}_6$ are stored and whose output supplies the desired value for further processing.

The subsequent circuits sum the values assigned to the individual points of an element, superposes the measuring values obtained from the individual measuring series, and stores the reconstructed image. The values assigned to three adjacent points are each time added in a loop connected around an adding device 29, having an input which is connected to the output of the intermediate storage 28, a single intermediate storage position 30, and a switch 31 which operates under the control of clock signals $\bar{t}_1$ and $\bar{t}_2$. When a first value is received the switch 31 being in the correct position, previous values are also added, (i.e. the value assigned to a set of three points of the same element in one or two previous lines, or the value assigned to an element on the basis of preceding measuring series). The value added is dependent upon the position of a second switch 32 which is connected between a contact of the switch 31 and the output of a shift register 33. The input of the shift register 33 is connected to the output of the intermediate store 30 (which may thus be considered as a storage position in the shift register 33).

When the value of a line of points has thus been obtained and transferred, under the control of the clock signal $t_2$, into the subsequent shift register 33 which comprises m-1-storage positions (m=number of elements of a line; so 4 in the present example) three successive lines are added by means of the clock signals $\bar{t}_2$ and $\bar{t}_3$ so that the value of the previous line is fed back to the adding device 29 via the switches 31 and 32. The combination of the 3×3 points to form one image element is thus performed without need for an additional storage position.

The complete line of image elements is stored in a shift register 34 (number of storage positions: n−m; n=number of elements of the image matrix) by means of the clock signal $t_3$. At the beginning of each line of elements, that is at the beginning of each third line of points, a stored value is returned from the shift register 34 to the adder 29, via the switches 31 and 32 and under the control of the clock signals $\bar{t}_2$, $\bar{t}_3$ and $t_3$ in order to superpose the absorption distribution obtained from the new measuring series on the absorption distributions obtained from previous measuring series. After completion of the superposition, the absorption distribution derived from the relevant measuring series is stored in the network formed by the shift registers 30, 33 and 34 (possibly after superposition of the previously obtained absorption distributions) and can be read. Before the beginning of a new reconstruction, that is to say when completely new measuring series have to be evaluated, obviously, the stores 30, 33 and 34 must be reset to zero. This is not separately shown in the circuit diagram.

FIG. 5 shows the variation in time of the clock signals $t_x$, $t_y$, $t_B$, $t_2$ and $t_3$. The clock signals $\bar{t}_B$, $\bar{t}_2$ and $t_3$ correspond to the signals $t_B$, $t_2$ and $t_3$, respectively; however, the individual pulses are wider, i.e. they start earlier and terminate later than in the clock signals without a stroke. The clock signal $t_1$ corresponds to the clock signal $t_x$, but is delayed with respect thereto, because the reading of a value $M_1 \ldots M_6$ from a line of the intermediate storage 28 cannot be effected simultaneously with the supply of the address of this storage position.

The references I-1 and I-2 in the time diagram of FIG. 5 denote two successive periods of the reconstruction of two complete images; L-1, L-2 . . . L-4 denote the periods of the reconstruction of a line of the image I-1 or I-2, and P denotes the reconstruction period of an image element.

Referring to the device shown in FIG. 4 and the diagram shown in FIG. 5, it is to be noted that the operation is only diagrammatically illustrated. In order to ensure a simple operation of the storage devices, normal steps known in the digital art must be taken. For example, a shift register comprising charge-coupled elements must be actuated by two clock pulse series, supplied to different inputs. The feeding back of a storage output to the preceding adding device (for example, the components 29 and 30) requires additional intermediate storage (not shown in the drawing) in order to prevent, in the case of a modification of an output quantity, the unambiguous state of the adding device from being disturbed before it is transferred into the storage. These problems, however, occur in all logic circuits, so that it not necessary to elaborate.

The device shown has the advantage that the subdivision of an element into different points is controlled only by clock signals. For example, if an element is to be sub-divided into a different number of points, for example, 4×4 points instead of 3×3 points, only the clock drive need be modified.

What is claimed is:

1. An improved device for computing and displaying the spatial distribution of physical characteristics in a layer of a body from signal values which are derived from measurements made by a radiation source and one or more radiation detectors in a multiplicity of measuring series along a corresponding multiplicity of directions in the layer comprising:
   an allocation device which, for each measuring series, assigns one of the signal values to each of a multiplicity of image points, each assigned signal value having been produced in the same strip in which the associated image point is situated;
   storage means connected to accumulate and store all of the assigned signal values for each image point;
   summing means connected to receive and superpose all of the signal values for each image point to produce a superposed value for that image point; and
   display means connected to receive the superposed values and to produce therefrom a display wherein the values of displayed points correspond to the mean-value of the superposed values of image points in the region of each displayed point.

2. A device as claimed in claim 1 wherein the number of said image points is at least four times greater than the number of signal values.

3. A device as claimed in claim 1 wherein the assigned signal values are stored in storage positions in the storage means, the values to be superposed from each measuring series being simultaneously read from the various storage positions and summed by reading and summing means to produce summed values, the summed value for each image point being displayed by the display means; the display means further functioning so that each of the displayed points at least partially overlaps neighboring displayed points.

4. A device as claimed in claim 1, 2 or 3 wherein the allocation device comprises:
   a computer which calculates the distance $\eta$ between a straight line through the image point parallel to the strips, and a reference point;

an intermediate storage device which stores the signal value in the strip in which the image point is situated; and an addressing device which forms, on the basis of the calculated distance, the address of an intermediate storage position and which assigns the contents thereof to the image point.

5. A device as claimed in claim 4 wherein the computer comprises:

two sawtooth generators connected to generate output voltages ($u_x$, $u_y$) which correspond to the position in a rectangular system of coordinates of an image point in the layer to be examined;

two multiplier circuits connected to respectively multiply the output voltages ($u_x$, $u_y$) by angle dependent factors which are determined from the angular position ($\theta$) of the strip; and an adding circuit connected to sum the outputs of the two multipliers.

6. A device as claimed in claim 5 wherein the adding circuit is further connected to sum a constant element ($\theta_0$) with the outputs of the two multipliers.

7. A device as claimed in claim 4 wherein the addressing device is an analog-to-digital converter connected for converting an analog signal representing the distance ($\eta$) into a digital signal and for eliminating least-significant bits of the digital signal.

8. A device as claimed in claim 1 for computing radiation absorption at discrete points, further comprising;

an adding device for adding the signal values assigned to adjacent image points to produce a sum value;

a storage device which functions to assign the sum value thus formed to that element of the layer to be examined which is defined by the adjacent image points; and a display device connected to display the sum values corresponding to individual regions of the layer.

* * * * *